(12) United States Patent
Stebbings

(10) Patent No.: US 9,267,956 B2
(45) Date of Patent: Feb. 23, 2016

(54) STIMULATED CELL STANDARDS

(75) Inventor: Richard John Stebbings, Potters Bar (GB)

(73) Assignee: SECRETARY OF STATE FOR HEALTH, London (GB)

( * ) Notice: Subject to any disclaimer, the term of this patent is extended or adjusted under 35 U.S.C. 154(b) by 526 days.

(21) Appl. No.: 13/003,661

(22) PCT Filed: Jul. 9, 2009

(86) PCT No.: PCT/GB2009/050815
§ 371 (c)(1),
(2), (4) Date: Apr. 11, 2011

(87) PCT Pub. No.: WO2010/004336
PCT Pub. Date: Jan. 14, 2010

(65) Prior Publication Data
US 2011/0183372 A1    Jul. 28, 2011

(30) Foreign Application Priority Data

Jul. 11, 2008 (GB) .................................. 0812755.7
Jul. 11, 2008 (GB) .................................. 0812757.3

(51) Int. Cl.
*G01N 33/96* (2006.01)

(52) U.S. Cl.
CPC .................................... *G01N 33/96* (2013.01)

(58) Field of Classification Search
CPC .......................... G01N 33/96; G01N 2496/05
USPC ........................................................ 435/40.5
See application file for complete search history.

(56) References Cited

U.S. PATENT DOCUMENTS 6,008,052 A * 12/1999 Davis et al. .................. 436/10
6,197,539 B1 * 3/2001 Granger et al. ............. 435/40.5

FOREIGN PATENT DOCUMENTS

WO    WO 03/020874 A2 *   3/2003
WO    WO 2007/094027 A2   8/2007

OTHER PUBLICATIONS

Nomura et al., "Optimization of Whole Blood Antigen-Specific Cytokine Assays for CD4+ T Cells", Cytometry 40 : 60-68 (2000).*
Rostaing et al., "Kinetics of Intracytoplasmic Th1 and Th2 Cytokine Production Assessed by Flow Cytometry Following In Vitro Activation of Peripheral Blood Mononuclear Cells", Cytometry 35 : 318-328 (1999).*
Cox, J. H. et al. 2005 "Results of an ELISPOT proficiency panel conducted in 11 laboratories participating in internation human immunodeficiency virus type 1 vaccine trials" *Aids Research and Human Retroviruses* 21(1):68-81.
Janetzki, S. et al. 2005 "Standardization and validation issues of the ELISPOT assay" *Methods in Molecular Biology* 302(1):51-86.
Maecker, H.T. et al. 2005 "Standardization of cytokine flow cytometry assays" *BMC Immunology* 6(1):13 (Epub).
Pinto, L.A. et al. 2005 "Fixation and cryopreservation of whole blood and isolated mononuclear cells: Influence of different procedures on lymphocyte subset analysis by flow cytometry" *Cytometry Part B (Clinical Cytometry)* 63B:47-55.
Suni, M.A. et al. 2003 "Performance of plate-based cytokine flow cytometry with automated data analysis" *BMC Immunology* 4(1):9 (Epub).

* cited by examiner

*Primary Examiner* — Robert Yamasaki
*Assistant Examiner* — Teresa E Knight
(74) *Attorney, Agent, or Firm* — Knobbe, Martens Olson & Bear, LLP

(57) ABSTRACT

Methods for producing stimulated, positive and negative control reference standard for monitoring intracellular cytokine levels and cytokine release in test samples by stimulating cells to produce cytokines in the presence of a cytokine release inhibitor, fixing the stimulated cells with a fixative such as paraformaldehyde, washing to remove excess fixatives and freeze-drying the stimulated, fixed cells. Methods for producing labeled reference standards for cell proliferation assays are also disclosed, in which proliferation-competent mammalian cells, isolated from a human or animal body are labeled with a label, such as a dye, that is divided between daughter cells during cell proliferation (e.g., carboxyfluorescein succinimidyl ester), the cells are stimulated to proliferate, the proliferated cells are fixed by addition of a fixative and then preserved by freeze drying or cryopreservation.

12 Claims, No Drawings

STIMULATED CELL STANDARDS

RELATED APPLICATIONS

This application is a U.S. National Phase of International Application No.: PCT/GB2009/050815, filed Jul. 9, 2009, designating the U.S. and published in English on Jan. 14, 2010 as WO2010/004336A2, which claims the benefit of United Kingdom Application No. 0812755.7, filed Jul. 11, 2008 and United Kingdom Application No. 0812757.3, filed Jul. 11, 2008.

FIELD OF THE INVENTION

The invention relates to standard control reference materials for use in cytokine and in cell proliferation assays. The invention also relates to methods for producing such materials.

BACKGROUND AND PRIOR ART KNOWN TO THE APPLICANT

The detection of cytokine release by ELISPOT assay and the quantification and identification of intracellular cytokines by flow cytometry are both widely used as indices of cell mediated immune responses. In the so-called ELISPOT assay, cytokines released from immobilised cells typically interact with an immunoassay, such as an ELISA assay, to produce a coloured "spot" on the assay plate providing both qualitative (e.g. type of immune protein) and quantitative (number or proportion of cells responding) information. The standardisation of these assays requires the development of reliable reference standards for monitoring intracellular cytokine levels and cytokine release in test samples, thus allowing comparability between different laboratories and assays.

Stimulated (cytokine positive), fixed, cryopreserved cells are available commercially for intracellular flow cytometry (Becton Dickinson, Oxford, UK), and freeze dried unstimulated cells are available either as controls for surface staining or for purposes of haematology analysis (Beckman Coulter UK Ltd, High Wycombe, UK).

For ELISPOT assays, or other assays where cytokine release from cells is monitored, only cryopreserved live cells from individual donors are currently available.

The presently-available approaches to the provision of a standardised reference material have a number of drawbacks: In order to standardise reference materials over a large number of laboratories world-wide, and to provide reference materials that may be used over many years, a large amount of stable material is required. However, live cells from multiple donors cannot be pooled to make large single batches due to mixed lymphocyte reactions, resulting in cell death and overexpression of cytokines.

Cryopreserved cells also require specialised storage using e.g. liquid nitrogen and shipment on dry ice, thus increasing costs. There is also the risk of thawing and refreezing during shipment, in the event of power failure to refrigeration devices, say, leading to deterioration of the material, so rendering it useless as a reference standard. Furthermore, cryopreserved cells must be carefully thawed to ensure consistency of responses. It has proven difficult to obtain consistent results between laboratories using this approach.

Measurement of cell proliferation in mammalian cells is also an important technique for e.g. the assessment of the effects of exogenous agents on a cell's ability or propensity to divide. For example, such assays may be used for detecting the marked proliferation of cells of the immune system following an immune response. A number of techniques are currently used wherein cells are labeled with a detectable marker that is shared between daughter cells following cell division.

One such technique uses the fluorescent dye carboxyfluorescein diacetate succinimidyl ester (CFSE or CFDA, SE). The technique is described by Lyons, B. in Immunol. Cell Biol 1999; 77(6):509-515 in which the author reports that "The technique can be used both in vitro and in vivo, allowing eight to 10 successive divisions to be resolved by flow cytometry. Furthermore, viable cells from defined generation numbers can be sorted by flow cytometry for functional analysis". Other techniques include the incorporation of bromodeoxyuridine or tritiated thymidine into the cells.

Whilst these assays are well known, a difficulty that arises is the provision of reference standards for cross-calibration and quality control when the assays are used across different analysis laboratories, or are used successively over long periods of time, e.g. during clinical longitudinal studies.

The lack of suitable reference materials for such cytokine and cell proliferation assays hinders robust testing methodologies, especially in respect of comparability between different laboratories and assays. It is amongst the objects of the present invention to attempt a solution to these problems.

SUMMARY OF THE INVENTION

Accordingly, in a first aspect, the invention provides a method of preparing cellular reference material comprising the steps of: (a) obtaining a cell sample, isolated from a human or animal body, said cell sample comprising cells selected from the group comprising: basophils, neutrophils, eosinophils, monoctytes, lymphocytes (B-lymphocytes and T-lymphocytes) and natural killer cells (all peripheral blood mononuclear cells, PBMC), thrombocytes and cell lines; (b) stimulating said cells to produce cytokines in the presence of a cytokine secretion inhibitor; (c) fixing said stimulated cells by addition of a fixative; (d) preserving said fixed stimulated cells by freeze drying.

By cell lines, we mean a cell culture capable of proliferation given appropriate fresh media and space, such cells being originally isolated from a human or animal body, and capable of cytokine production. Such cells may either produce cytokines inherently, or may be modified to include exogenous genetic material coding for, and leading to synthesis of, one or more cytokines, e.g. including but not restricted to TNF-α, IFN-γ, IL-1 and IL-6. Exogenous DNA may be introduced into a recipient eukaryote cell by, say, micro-injection, electroporation, the use of calcium phosphate or a liposomal transfection reagent, and said genetic material may be subsequently integrated into the chromosomal DNA of said cells, or may remain present as e.g. a plasmid. For cells that are capable of producing cytokines inherently, such cells may be modified, e.g. by the introduction of promoter sequences to upregulate cytokine production. Cells may be stimulated if required, e.g. by use of a mitogen, to produce cytokines and preserved according to the technique(s) described herein.

Transduction of a cytokine gene into neoplastic cells is known to elicit a strong inflammatory host reaction (see e.g. "The boosting effect of co-transduction with cytokine genes on cancer vaccine therapy using genetically modified dendritic cells expressing tumor-associated antigen", International journal of oncology; OJIMA Toshiyasu et al: ISSN 1019-6439 2006, vol. 28, no4, pp. 947-953). In vivo, this impairs tumour growth. In vitro, intra-cellular cytokines may be preserved according to the technique(s) described herein.

Such cell lines may include cell lines derived from basophils, neutrophils, eosinophils, monocytes, lymphocytes (B-lymphocytes and T-lymphocytes), natural killer cells (all peripheral blood mononuclear cells, PBMC) and thrombocytes, or cell lines such as HeLa, HL-60, A-549, Jurkat, LNCap and CAPAN-1 cells.

In preferred embodiments, the invention provides a method of preparing cellular reference material comprising the steps of: (a) obtaining a cell sample, isolated from a human or animal body, said cell sample comprising cells selected from the group comprising: basophils, neutrophils, eosinophils, monoctytes, lymphocytes (B-lymphocytes and T-lymphocytes) and natural killer cells (all peripheral blood mononuclear cells, PBMC), and thrombocytes; (b) stimulating said cells to produce cytokines in the presence of a cytokine secretion inhibitor; (c) fixing said stimulated cells by addition of a fixative; (d) preserving said fixed stimulated cells by freeze drying.

In a second independent aspect, the invention also provides a method of preparing cellular reference material comprising the steps of: (i) obtaining a mixed cell population, isolated from a human or animal body, said mixed cell population comprising a plurality of cell types selected from the group comprising: peripheral blood mononuclear cells; thrombocytes; (ii) fractionating said mixed cell population to produce a plurality of fractions having distinct populations of cell types within each fraction; (iii) stimulating cells within one or more of said fractions to produce cytokines in the presence of a cytokine secretion inhibitor; (iv) fixing said cells within each fraction by addition of a fixative; (v) recombining a plurality of said fractions to produce a mixture of differentially-stimulated cells; (vi) preserving said mixture of differentially-stimulated cells by freeze-drying or cryopreservation.

In this way, reference standards mimicking a particular pattern of cytokine expression in different cell types may be produced. Such cytokine expression standards would provide a benefit in both the clinical and research setting by assisting in both the diagnosis/prognosis of potential disease states and in the analysis of material/experimental outcomes within the research laboratory/empirical setting.

In either aspect of the invention it is preferred that said cell sample is isolated from a mammalian body, and more preferably from a human body.

Also in any aspect of the invention, it is preferred that said cells are stimulated by the addition of a mitogen. Preferably, and in particular for intracellular cytokine staining, said mitogen comprises PMA (phorbol-12-myristate-13-acetate). Preferably also, said mitogen comprises Ionomycin. More preferably, said mitogen comprises a mixture of PMA (phorbol-12-myristate-13-acetate) and Ionomycin. Preferably also, and in particular for use in Elispot assays, said mitogen comprises a mixture of PHA (Phyto-hemagglutinin), IL-2 (interleukin-2) and co-stimulatory anti-human CD28 monoclonal antibody.

Also in any aspect of the invention it is preferred that said cytokine secretion inhibitor comprises Brefeldin A.

Also in any aspect of the invention it is preferred that said fixative comprises paraformaldehyde. Preferably, said fixative comprises a mixture of paraformaldehyde and chromium chloride. Fixation has the benefit of suspending intra- and extra-cellular biological activity, including apoptosis, thus improving the biological and structural integrity of the cells during the freeze-drying process.

Also in any aspect of the invention the method further comprises the step of removing residual fixative after fixing said cells and before preserving said cells. This allows cells to be used immediately upon reconstitution without additional washing step to remove fixatives. One benefit of this step is that it minimises volumetric variation of cell numbers. Excess fixative can cause non-specific staining and prevent the release of cytokines in ELISPOT assays.

Also in any aspect of the invention the method further comprises the step of exposing said fixed cells to hypertonic conditions prior to preserving said cells. By processing the cells in their hypohydrated state, the cells become physically more resilient and thus strengthened—the overall yield of reference material is increased.

Also in any aspect of the invention the method further comprises the step of adding a cryoprotectant to said fixed cells prior to freeze-drying said cells. The addition of a cryoprotectant has the benefit of improving the structural integrity of the cells during the freeze-drying process.

Overall, among the benefits provided by the present invention are that:

(i) although the reference cells so produced are optimally stable at +4° C., the cells can be shipped at ambient temperature without degradation;

(ii) the cells are easily reconstituted with distilled water;

(iii) the cells function both in flow cytometry assays, and also in ELISPOT assays, the cells releasing their cytokines to the surrounding environment, particularly when held at an elevated temperature, around 37° C.

Also included in the scope of the invention is a method of preparing cellular reference material comprising the steps of: obtaining a plurality of cell samples isolated from a plurality of individuals; carrying out a method described above on each cell sample; and further comprising the step of combining fixed cells derived from a plurality of said samples prior to preserving said cells. This has the added benefit of allowing large batches from pooled donors to be prepared and stored, since the methods described herein obviate any mixed lymphocyte reactions which would otherwise result from pooling live cells. Thus, large quantities of standardized reference material may be produce, which has hitherto not been possible.

Also included in the scope of the invention is a method of preparing cellular reference material comprising the steps of: obtaining a plurality of mixed cell populations isolated from a plurality of individuals; carrying out a method described above, according to the second aspect of the invention, on each mixed cell population; and further comprising the step of combining fixed cells derived from a plurality of said mixed cell populations prior to preserving said cells. This has the added benefit of allowing the synthesis/production of mixed lymphocyte populations which both quantitively and qualitatively mimic the mixed lymphocyte populations found in various disease states. For example, with the onset of Graves disease, thyrocytes express cytokines they normally would not, such as TNF-α, IFN-γ, IL-1 and IL-6.

Also included in the scope of the invention is a method of preparing cellular reference material comprising the steps of: preparing unstimulated fixed cells according to the method steps of any preceding aspect in which the stimulation step (b) or (iii) is omitted; combining said unstimulated fixed cells with stimulated fixed cells prepared according to the method steps of any preceding aspect; and preserving said combined cells by freeze drying or cryopreservation. This has the added benefit of providing mixed lymphocyte populations which mimic the non-diseased state as a comparator for disease-state populations, i.e. to act as a negative control.

In a further independent aspect, the invention also provides a method of preparing cellular reference material comprising the steps of: (i) obtaining a mixed cell population, isolated from a human or animal body, said mixed cell population comprising a plurality of cell types selected from the group comprising: peripheral blood mononuclear cells; thrombocytes; (ii) fractionating said mixed cell population to produce a fraction having predominantly a single cell type within said fraction; (iii) labeling cells within said fraction; (iv) fixing the labeled cells within said fraction by addition of a fixative; and (v) preserving said labeled cells by freeze-drying.

For example, CD4+ cells may be isolated from PBMC using immuno-magnetic sorting, stained with an anti-CD4 antibody labeled with FITC (fluorescein isothiocyanate) and freeze-dried following fixation as described herein. Such cells may be used as reference standard for e.g. fluorescence calibration of flow cytometry apparatus.

In a further aspect, the invention provides a method of preparing cellular reference material comprising the steps of: (a) obtaining proliferation-competent mammalian cells, isolated from a human or animal body; (b) labeling said cells with a label that is divided between daughter cells during cell proliferation; (c) stimulating said labeled cells to proliferate; (d) allowing said cells to proliferate; (d) fixing said proliferated cells by addition of a fixative; and (e) preserving the resultant cells by freeze drying or cryopreservation.

Preferably, said cells are preserved by freeze-drying. Although useful, cryopreserved cells require specialised storage using e.g. liquid nitrogen and shipment on dry ice, thus increasing costs. There is also the risk of thawing and re-freezing during shipment, in the event of power failure to refrigeration devices, say, leading to deterioration of the material, so rendering it useless as a reference standard. Furthermore, cyropreserved cells must be carefully thawed to ensure consistency of responses. Freeze-drying therefore provides considerably more stable reference materials. Fixation of the cells has the benefit of suspending intra- and extra-cellular biological activity, including apoptosis, thus improving the biological and structural integrity of the cells during the freeze-drying process.

Preferably, said cells are isolated from a mammalian body, and more preferably said cells are isolated from a human body.

In any aspect of the invention where said cells comprise proliferation-competent mammalian cells, it is preferred that said cells are stimulated by the addition of a mitogen. Preferably, said mitogen comprises PMA (phorbol-12-myristate-13-acetate). Preferably also, said mitogen comprises Ionomycin. More preferably, said mitogen comprises a mixture of PMA (phorbol-12-myristate-13-acetate) and Ionomycin. In alternative embodiments, stimulation of proliferation may be carried out by addition of a mitogenic monoclonal antibody such as UCHT1.

Also in any aspect of the invention where said cells comprise proliferation-competent mammalian cells, it is preferred that said fixative comprises paraformaldehyde. More preferably, said fixative comprises a mixture of paraformaldehyde and chromium chloride.

Also in any aspect of the invention where said cells comprise proliferation-competent mammalian cells, it is preferred that the method further comprises the step of removing residual fixative after fixing said cells and before preserving said cells. This allows cells to be used immediately upon reconstitution, or thawing, without an additional washing step to remove fixatives. A benefit of this stage is that it volumetric variation of cell numbers. Excess fixative can cause non-specific staining of the cell suspension.

Also in any aspect of the invention where said cells comprise proliferation-competent mammalian cells, it is preferred that the method further comprises the step of exposing said fixed cells to hypertonic conditions prior to preserving said cells. By processing the cells in their hypohydrated state, the cells become physically more resilient and thus strengthened—the overall yield of reference material is increased.

Also in any aspect of the invention where said cells comprise proliferation-competent mammalian cells, it is preferred that the method further comprises the step of adding a cryoprotectant to said fixed cells prior to preserving said cells. The addition of a cryoprotectant has the benefit of improving the structural integrity of the cells during the freeze-drying or cryopreservation process.

Also in any aspect of the invention where said cells comprise proliferation-competent mammalian cells, it is preferred that said cells are labeled with a fluorescent label. More preferably, said fluorescent label comprises CFSE (carboxyfluorescein succinimidyl ester).

Also included within the scope of the invention is a method of preparing cellular reference material substantially as described herein.

DESCRIPTION OF PREFERRED EMBODIMENTS

Example 1

Production of Stimulated Cell Standards

In one embodiment of the invention, "buffy coats" are obtained e.g from phlebotomised donors or a national blood collection agency. The buffy coat fraction of blood is that portion of blood that, following centrifugation, contains the majority of the white blood cells and platelets. All such obtained buffy coats will typically be tested to ensure they are negative for *Treponema pallidum* haem-agglutination test ("TPHA"), Hepatitis B surface antigent ("HBsAg"), anti Human Immunodeficiency Virus 1 ("anti-HIV1"), anti-Human Immunodeficiency Virus 2 ("anti-HIV 2") and anti Hepatitis C Virus ("anti-HCV") prior to use.

Residual erythrocytes contained within the buffy coats are removed by application of any standard, commercially available lymphocyte density gradient preparation, such as Lymphoprep, and peripheral blood mononuclear cells ("PBMC") are subsequently isolated/collected, again by application of a lymphocyte density gradient preparation. The PBMC are then washed in a mammalian cell culture medium such as RPMI 1640 media.

For production of stimulated reference standards (as opposed to an unstimulated, negative control standard) the PMBC are immuno-stimulated using T-cell stimulating mitogens, typically within an environment containing 4-6% carbon dioxide, and at a temperature of 36-38° C. In preferred embodiments, a combination of immuno-stimulants are used, said stimulants commonly comprising phorbol 12-myristate 13-acetate (PMA) (applied at a concentration of 0.01-0.03 µg per ml, say 0.02 µg per ml) and Ionomycin (applied at a concentration of 0.125-0.165 µg per mg, say 0.145 µg per mg). The stimulation technique is suitable for cytokine-production, and if immuno-stimulated for 4-6 hours, cytokine production within the cells PMBC is detectable.

The PMBC are simultaneously combined with a commercially available extra-cellular protein transport inhibitor, such as Brefeldin A or Monensin, which results in cytokine accumulation within the said PMBC. If Brefeldin A is used, it would commonly be applied at a concentration of 9.0-11.0 µg per ml, say 10 µg per ml.

Following stimulation, the PBMC are washed in a combination of foetal calf serum ("FCS") and phosphate buffered saline ("PBS"), the FCS being used typically at a concentration of 9-12% v/v, say 10% and the PBS typically being double strength.

The washed PBMS are then re-suspended in a buffered culture medium (again comprising double strength PBS and 9-12% FCS), with the addition of 0.1-20% (v/v) of a commercially available transport fixative containing a combination of paraformaldehyde (0.1-0.2% w/v) and chromium chloride (0.5% w/v) in 0.85% (w/v) PBS. An example of one such fixative is known by the trade name "TransFix". The buffered culture medium and fixative is applied to the said PBMC at a rate of $8 \times 10^6$ PBMC per ml.

For production of unstimulated, negative control cells, PBMC are fixed immediately following isolation in paraformaldehyde and chromium chloride, as described above, and stored until required at +4° C.

Following stimulation and fixing (or just fixing, for negative control standards), the PBMC are subsequently washed with chilled (+4° C.) freeze drying buffer (a cryoprotectant). A typical buffer would comprise a double volume of 10% protein, typically, foetal calf serum or albumin in double strength PBS. The use of a freeze drying buffer improves PBS stability during the subsequent freeze drying process. These cells may then be stored at chill temperatures (typically +4° C.) before freeze-drying. In order to optimise the quality and consistency of the reference standards, the shelves of a freeze dryer are pre-cooled in order to maintain a temperature of +4° C. during the loading process.

After fixing, cells from a plurality of donors may be mixed together to increase the total volume of reference material so produced. The process of fixing allows cells from different donors to be mixed together without causing lymphocyte cross-reactions. Furthermore, fixed stimulated cells may be mixed with fixed, unstimulated cells (which can also be used as negative controls) in order to produce a cell population demonstrating typical levels of cytokine stimulation or for a minimum potency positive control.

The stimulated (or unstimulated), fixed cells are loaded into aliquots/capped vials. A filling machine such as one sold under the trade name Paxal, is suitable for large scale aliquoting.

After loading into the freeze dryer, the PBMC are freeze-dried, typically over a 5-day cycle. Residual moisture content after freeze drying is typically 0.35%.

Once fixative has been washed from the stimulated cells, the PBMC begin to leak cytokines, albeit slowly at low temperatures. Therefore, loading into aliquots and freeze drying of PBMC is performed within a few hours of fixative removal.

Following freeze-drying, the lyophilised reference materials may be stored for extended periods of time without degradation. The freeze-dried samples may be reconstituted in twice the starting volume of distilled water. This typically gives cells in single-strength phosphate buffered saline.

In a further embodiment of the invention, fractions of cells rich in a particular cell type may be isolated from a mixed population of PMBC and subjected to the stimulation and fixing regime described above before being re-combined with fixed, unstimulated cells.

In this way, cell populations with different levels of cytokines in specific cell types may be produced to mimic particular disease states. Particular cell types may be isolated by a number of means such as flow cytometry and cell-sorting, or by the use of antibody-linked magnetic beads, available commercially. Such separation techniques may be used to isolate e.g. B cells, monocytes, natural killer cells, neutrophils, platelets, etc., as well as particular subsets such as CD4 and CD8 T-cells. Again, such populations of differentially-stimulated cells may be diluted with unstimulated, fixed cells to produce cell populations that are a closer mimic to those found in particular disease states.

Cell reference standards produced according to methods of the invention may be reconstituted by addition of water, and used in cytokine assays. The cells retain surface antigens, as well as intracellular cytokines. They may be subjected, therefore, to staining techniques used in the art and used as reference standards for e.g. flow cytometry. Furthermore, the cells remain intact, and yet capable of releasing cytokines into their immediate environment, especially when held at elevated temperatures, e.g. 37° C., as commonly used in ELISPOT assays. They may therefore be used as reference standards in this type of assay.

Storage trials have demonstrated that the lyophilised cells retain their properties after storage for 5 months, with indications that they have a shelf life of many years, allowing them to be used as repeatable standards for long-term studies and diagnosis.

As well as being useful as reference standards, the freeze-dried cells produced by the methods described herein can also find use as vaccines as the cells' surface antigens are maintained in an intact state by the fixing and freeze drying process.

Example 2

Production of Cell Proliferation Standards

By way of an example, the methods disclosed herein may be used to produce reference standards for assay of proliferation of peripheral blood mononuclear cells (PBMC). In one embodiment of the invention, "buffy coats" are obtained e.g from phlebotomised donors or a national blood collection agency. The buffy coat fraction of blood is that portion of blood that, following centrifugation, contains the majority of the white blood cells and platelets. All such obtained buffy coats will typically be tested to ensure they are negative for *Treponema pallidum* haem-agglutination test ("TPHA"), Hepatitis B surface antigent ("HBsAg"), anti Human Immunodeficiency Virus 1 ("anti-HIV1"), anti-Human Immunodeficiency Virus 2 ("anti-HIV 2") and anti Hepatitis C Virus ("anti-HCV") prior to use.

Residual erythrocytes contained within the buffy coats are removed by application of any standard, commercially available lymphocyte density gradient preparation, such as Lymphoprep, and peripheral blood mononuclear cells ("PBMC") are subsequently isolated/collected, again by application of a lymphocyte density gradient preparation. The PBMC are then washed in a mammalian cell culture medium such as RPMI 1640 media.

These PBMC are then labeled with a fluorescent dye such as the commercially-available carboxyfluorescein succinimidyl ester ("CFSE") or carboxyfluorescein succinimidyl ester ("CFDA-SE"). An example of one such dye is known by the trade name CellTrace CFSE Cell proliferation Kit. The labeled cells are then stimulated to induce proliferation for 70-74 hours with the monoclonal antibody UCHT1, prior to being stabilized with a fixative and freeze-dried or cryopreserved. Stimulation is typically carried out within an environment containing 4-6% carbon dioxide, and at a temperature of 36-38° C. This stimulation induces cell proliferation. In other embodiments, a combination of immuno-stimulants are used, said stimulants commonly comprising phorbol 12-myristate 13-acetate (PMA) (applied at a concentration of 0.01-0.03 μg per ml, say 0.02 μg per ml) and Ionomycin (applied at a concentration of 0.125-0.165 μg per mg, say 0.145 μg per mg). Following such stimulation, proliferation takes place within typically 70-74 hours.

Following proliferation to the degree required (depending on the reference material to be produced), the PBMC are washed in a combination of foetal calf serum ("FCS") and phosphate buffered saline ("PBS"), the FCS being used typically at a concentration of 9-12% v/v, say 10% and the PBS typically being double strength.

The washed PBMS are then re-suspended in a buffered culture medium (again comprising double strength PBS and 9-12% FCS), with the addition of 20% (v/v) of a commercially available transport fixative containing a combination of paraformaldehyde (0.1-0.2% w/v) and chromium chloride (0.5% w/v) in 0.85% (w/v) PBS. An example of one such fixative is known by the trade name "TransFix". The buffered culture medium and fixative is applied to the said PBMC at a rate of $8 \times 10^6$ PBMC per ml.

After fixing, the PBMC are subsequently washed with chilled (+4° C.) freeze drying buffer (a cryoprotectant). A typical buffer would comprise a double volume of 10% protein, typically, foetal calf serum or albumin in double strength PBS. The use of a freeze drying buffer improves PBMC stability during the subsequent freeze drying process. These cells may then be stored at chill temperatures (typically +4° C.) before freeze-drying. In order to optimise the quality and consistency of the reference standards, the shelves of a freeze dryer are pre-cooled in order to maintain a temperature of +4° C. during the loading process.

The labeled, proliferated, fixed cells are then loaded into aliquots/capped vials. A filling machine such as one sold under the trade name Paxal, is suitable for large scale aliquoting.

After loading into the freeze dryer, the PBMC are freeze-dried, typically extended over a 5-day cycle. Residual moisture content after freeze drying is typically 0.35%.

Following freeze-drying, the lyophilised reference materials may be stored for extended periods of time without degradation. The freeze-dried samples may be reconstituted in twice the starting volume of distilled water. This typically gives cells in single-strength phosphate buffered saline.

In a further embodiment of the invention, fractions of cells rich in a particular cell type may be isolated from a mixed population of PMBC and subjected to the labeling, proliferation and fixing regime described. In this way, cell populations with different degrees of proliferation in specific cell types may be produced. Particular cell types may be isolated by a number of means such as flow cytometry and cell-sorting, or by the use of antibody-linked magnetic beads, available commercially. Such separation techniques may be used to isolate e.g. B cells, monocytes, natural killer cells, neutrophils, platelets, etc., as well as particular subsets such as CD4 and CD8 T-cells. Again, such populations of differentially-proliferating cells may be diluted with labeled, "un-proliferated" fixed cells to produce cell populations that are a closer mimic to those found in particular disease states.

Cell reference standards produced according to methods of the invention may be reconstituted by addition of water, and used as reference standards for cell proliferation assays. The cells retain surface antigens suitable for subset analysis. They may be subjected, therefore, to staining techniques used in the art and used as reference standards for e.g. flow cytometry.

Storage trials have demonstrated that the lyophilised cells retain their properties after storage for 5 months, with indications that they have a shelf life of many years, allowing them to be used as repeatable standards for long-term studies and diagnosis.

The invention claimed is:

1. A method of preparing cellular reference material comprising:
   (a) obtaining a cell sample, isolated from a human or animal body, said cell sample comprising cells selected from the group consisting of:
   peripheral blood mononuclear cells;
   cell lines; and
   thrombocytes;
   (b) stimulating said cells to produce cytokines in the presence of a cytokine secretion inhibitor;
   (c) fixing said stimulated cells by addition of a fixative;
   (d) exposing said fixed cells to hypertonic conditions; and
   (e) preserving said fixed stimulated cells by freeze drying.

2. A method according to claim 1, wherein said cell sample is isolated from a mammalian body.

3. A method according to claim 2, wherein said cell sample is isolated from a human body.

4. A method according to claim 1, wherein said cells are stimulated by the addition of a mitogen.

5. A method according to claim 4 wherein said mitogen comprises PMA (phorbol-12-myristate-13-acetate).

6. A method according to claim 4 wherein said mitogen comprises Ionomycin.

7. A method according to claim 4 wherein said mitogen comprises a mixture of PMA (phorbol-12-myristate-13-acetate) and Ionomycin.

8. A method according to claim 1, wherein said cytokine secretion inhibitor comprises Brefeldin A.

9. A method according to claim 1, wherein said fixative comprises paraformaldehyde.

10. A method according to claim 9 wherein said fixative comprises a mixture of paraformaldehyde and chromium chloride.

11. A method of preparing cellular reference material comprising:
    (a) obtaining a plurality of cell samples isolated from a plurality of individuals,
    said plurality of cell samples comprising cells selected from the group consisting of peripheral blood mononuclear cells, cell lines and thrombocytes;
    (b) stimulating each of said cell samples to produce cytokines in the presence of a cytokine secretion inhibitor;
    (c) fixing said stimulated cell samples by addition of a fixative;
    (d) combining the fixed cell samples; and
    (e) preserving said fixed stimulated cells by freeze drying.

12. A method of preparing cellular reference material the method consisting essentially of:
    (a) obtaining an unstimulated cell sample, isolated from a human or animal body, said cell sample comprising cells selected from the group consisting of:
    peripheral blood mononuclear cells;
    cell lines; and
    thrombocytes;
    (b) fixing said unstimulated cells by addition of a fixative;
    (c) combining said unstimulated fixed cells with stimulated fixed cells prepared according to steps (a)-(d) of the method of claim 1; and
    (d) preserving said combined cells by freeze drying or cryopreservation.

* * * * *